United States Patent [19]
Kagawa et al.

[11] Patent Number: 5,958,885
[45] Date of Patent: Sep. 28, 1999

[54] PEPTIDE AND FORMULATIONS THEREOF INHIBITING ELEVATIONS OF TRIGLYCERIDE LEVELS IN BLOOD

[75] Inventors: Kyoichi Kagawa; Hisako Matsutaka; Chizuko Fukuhama; Hiroaki Fujino, all of Osaka; Masahiro Numata, Ibaraki; Kazuhisa Honda, Ibaraki; Toyoo Nakamura, Ibaraki, all of Japan

[73] Assignees: Hankyu Kyoei Bussan Co., Ltd., Osaka; Itoham Foods Inc., Hyogo, both of Japan

[21] Appl. No.: 08/973,539

[22] PCT Filed: Jun. 10, 1996

[86] PCT No.: PCT/JP96/01570

§ 371 Date: Nov. 24, 1997

§ 102(e) Date: Nov. 24, 1997

[87] PCT Pub. No.: WO97/35875

PCT Pub. Date: Oct. 2, 1997

[30] Foreign Application Priority Data

Mar. 22, 1996 [JP] Japan .................................. 8-066916

[51] Int. Cl.$^6$ ............................... C07K 5/10; C07K 7/04; A61K 38/00
[52] U.S. Cl. ........................... 514/18; 530/330; 530/338; 530/343; 530/344; 426/7; 426/52; 426/53; 426/54; 426/55; 426/56; 514/2; 514/21; 514/909; 435/71.1
[58] Field of Search ........................... 426/656; 530/330, 530/338; 514/18, 2, 21; 435/71.1

[56] References Cited

U.S. PATENT DOCUMENTS 5,723,443  3/1998  Kagawa et al. ........................... 514/18
5,756,467  5/1998  Kagawa et al. ........................... 514/18

FOREIGN PATENT DOCUMENTS 7-188284  7/1995  Japan ............................... C07K 7/06
06970     8/1989  WIPO .

OTHER PUBLICATIONS

Kagawa et al. "Acidic Protease Hydrolysate Inhibits Dietary Hypertriglyceridemia and Val–Val–Tyr–Pro, One of its Constituents Possesses Most Superior Effect". Life Sciences, 58, No. 20, pp. 1745–1755 (Apr. 12, 1996).

*Primary Examiner*—F. T. Moezie
*Attorney, Agent, or Firm*—Davidson, Davidson & Kappel, LLC

[57] ABSTRACT

The present invention relates to a peptide having an amino acid sequence of Val-Val-Tyr-Pro as well as an agent for inhibiting elevation of triglyceride levels in blood, a food for specified health use (the so-called physiologically functional food) and a feed comprising the above peptide as an active component. According to the present invention, a peptide inhibiting elevation of triglyceride levels in blood as well as an agent for inhibiting elevation of triglyceride levels in blood, a physiologically functional food and a feed, all comprising the peptide as an active component are obtained. With these products of the invention, it becomes possible to prevent or treat obesity and hyperlipemia of human and animals as well as circulatory system diseases such as hypertension and arteriosclerosis associated therewith. Furthermore, the materials of the invention make it possible to improve the meat quality of livestock and hatchery fish.

10 Claims, 3 Drawing Sheets

Gel Chromatogram of Globin Proteolysate

Reversed Phase Chromatogram (Acidic) of GD

Reversed Phase Chromatorogram (Neutral) of GD

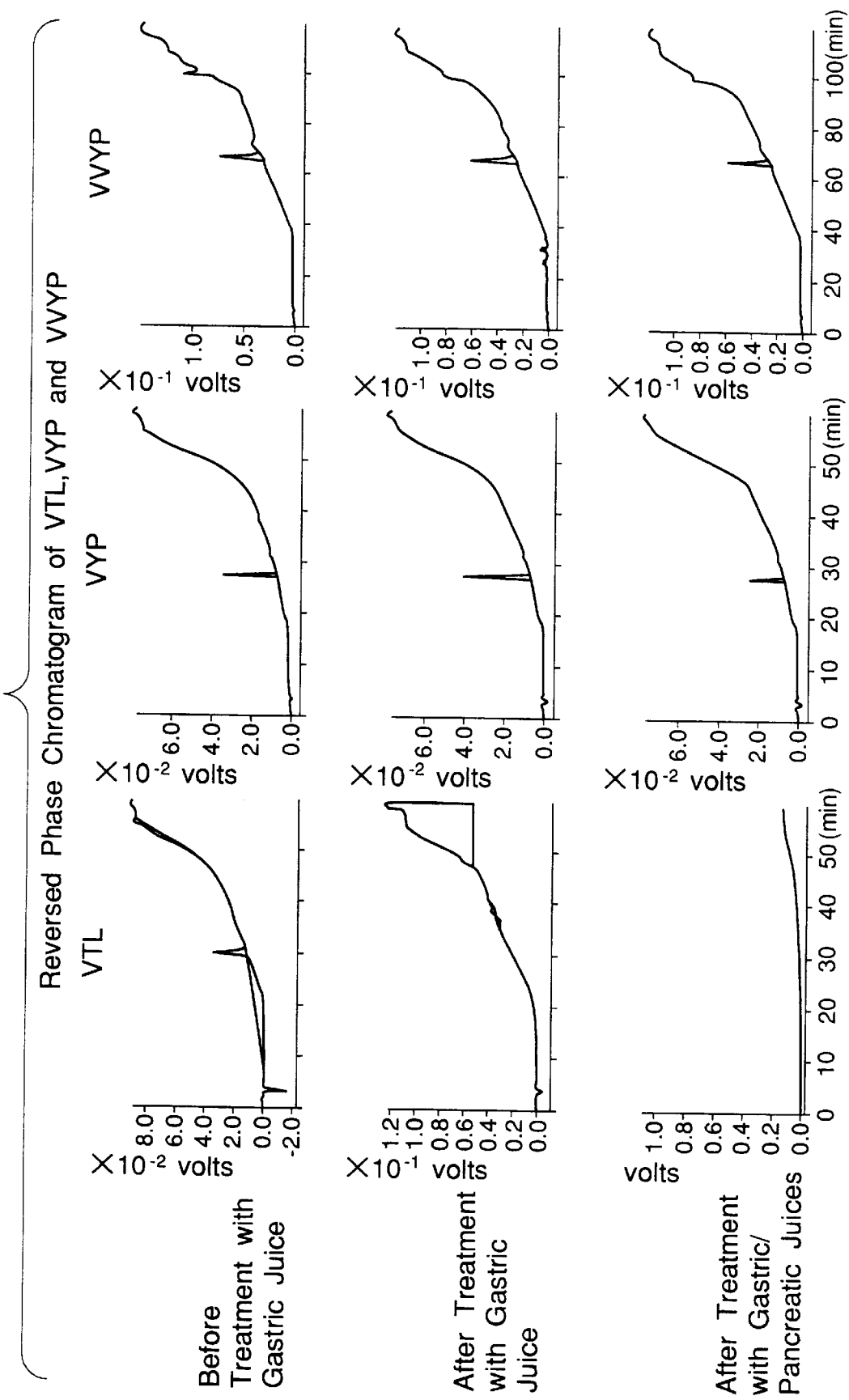

PEPTIDE AND FORMULATIONS THEREOF INHIBITING ELEVATIONS OF TRIGLYCERIDE LEVELS IN BLOOD

TECHNICAL FIELD

The present invention relates to a novel peptide inhibiting elevations of triglyceride levels in blood; an agent for inhibiting elevations of triglyceride levels in blood comprising the peptide as an active component; a food for specified health use (the so-called physiologically functional food) endowed with a function of inhibiting elevations of triglyceride levels in blood; and a feed endowed with a function of inhibiting elevations of triglyceride levels in blood.

BACKGROUND

Excessive intake of fat and sugar is known to cause obesity, hyperlipemia and the like. Elevations of triglyceride (hereinafter, sometimes referred to as "TG") levels in blood in hyperlipemia are said to become a cause which brings disorders such as hypertension and arteriosclerosis. Then, a number of attempts to inhibit elevations of TG levels in blood have been made to improve obesity and hyperlipemia.

At present, in order to inhibit elevations of TG levels in blood, dietary restriction, intake of dietary foods (such as low calorie diet (LCD) or very low calorie diet (VLCD)) and administration of various pharmaceuticals are carried out. As such pharmaceuticals, for example, dextran sulfate which enhances lipoprotein lipase activity in blood, nicomol which inhibits lipid absorption, clofibrate and pravastatin which are lipid metabolism improving agents, and the like are used.

However, dietary restriction gives anguish to those who practice it and side effects caused by the administration of the above pharmaceuticals are also apprehended. Thus, development of an agent for inhibiting elevations of blood TG levels is desired which has a stronger effect of inhibiting elevations of blood TG levels and in which there is no apprehension about causing side effects.

On the other hand, at present, high calorie feeds are given to livestock and hatchery fish for promoting their growth. As a result, abnormalities in fat metabolism occur also in such livestock and fish, and TG levels in their blood tend to elevate. Due to these elevations of TG levels in blood, fat contents in livestock and hatchery fish become excessive. Thus, eating such livestock or fish leads to excessive fat intake. Furthermore, such livestock and fish have gradually failed to meet consumers' liking in taste. In addition, the increase in fat contents described above is a serious issue relating to a problem of waste of feeds and also relating to a problem of disposal of the fat attached to slaughtered bodies. Thus, inhibition of elevations of TG levels in blood has become an urgent need, in particular, in the stockbreeding industry and the fisheries industry in Japan.

Recently, a patent application has been filed for an oligopeptide-containing material developed by some researchers including one of the present inventors (International Publication No. WO420979A1; Japanese Patent Publication No. 5-87052), and a technology similar to this is disclosed in Japanese Unexamined Patent Publication No. 2-154693. Also, it has been made clear that specific oligopeptides have lipid metabolism improving effects including inhibition of elevations of TG levels in blood (Kyoichi Kagawa, Food Chemical Monthly, 6:80 (1990); Chizuko Fukuhama et al., FOLIA PHARMACOLOGICA JAPONICA, 97:38 (1991)).

The oligopeptide-containing material disclosed in the above patent publication, etc. is a mixture of proteolysates and, thus, an amino acid sequence for its truly active component (i.e., a peptide as its active component) has not yet been elucidated.

This suggests that the above peptide-containing material is low in purity as a pharmaceutical. Further, when this material is combined in a food, it is difficult to quantitatively determine the material separately from other peptides contained in the food and thus there is a problem of quality control. Therefore, it is necessary to ascertain the truly active component in the above peptide-containing material, i.e., the peptide inhibiting elevations of TG levels in blood as an active component.

Although Japanese Unexamined Patent Publication No. 7-188284 discloses a peptide inhibiting elevations of triglyceride levels in blood and an agent for inhibiting elevations of triglyceride levels in blood comprising the above peptide, the effect of inhibiting elevations of triglyceride levels in blood produced by the peptide or the agent is still insufficient.

SUMMARY

It is an object of the present invention to analyze the amino acid sequence for the above-described peptide which is high in activity as an active component and also to provide an agent for inhibiting elevations of triglyceride levels in blood comprising the peptide as an active component; a physiologically functional food endowed with a function of inhibiting elevations of triglyceride levels in blood; and a feed endowed with a function of inhibiting elevations of triglyceride levels in blood.

As a result of intensive and extensive researches toward the solution of the above assignment, the present inventors have found that the above assignment can be solved by the invention described below.

The present invention relates to a peptide having the amino acid sequence shown in SEQ ID NO: 1.

The present invention also relates to an agent for inhibiting elevations of triglyceride levels in blood, a food for specified health use and a feed, all comprising a peptide hating the amino acid sequence shown in SEQ ID NO: 1. as an active component.

DETAILED DESCRIPTION

The peptide of the invention has the amino acid sequence shown in SEQ ID NO: 1. This peptide can be separated and purified from a protein occurring in nature. Alternatively, it can be chemically synthesized directly by known methods. It is also possible to prepare the peptide of the invention by engineering a gene having a base sequence corresponding to the above peptide sequence, inserting the gene into an appropriate expression vector, and expressing the gene in an appropriate host.

By using the peptide of the invention, it is possible to prevent or inhibit elevations of triglyceride levels in blood. Such prevention or inhibition makes it possible to prevent or treat human or animal obesity and hyperlipemia as well as cardiovascular diseases such as hypertension and arteriosclerosis associated therewith. Furthermore, with the peptide of the invention, it is possible to improve the meat quality of livestock and hatchery fish.

This peptide of the invention can be used as an agent for inhibiting elevations of triglyceride levels in blood, an agent for preventing or inhibiting obesity, an agent for preventing or treating hyperlipemia, and the like.

A. Method for Preparing the Peptide of the Invention

The peptide of the invention can be obtained, for example, by the methods as described below.

A-1. Method for Separating and Purifying the Peptide of the Invention from a Protein Occurring in Nature As a raw material for preparing the peptide of the invention, an animal protein such as fish meat protein, fish powder, globin, etc. or a plant protein such as corn protein (zein), soybean protein, etc. may be used widely. Among these proteins, globin proteins such as hemoglobin and myoglobin are especially preferable in that they can strongly produce the desired effect of inhibiting elevations of TG levels in blood. The kind of animal as a source of this globin protein is not particularly limited. Blood from bovine, porcine, sheep, human, eguine, etc. may be used widely.

In order to obtain the peptide of the invention, first, the above-mentioned protein is hydrolyzed. Operations for this hydrolysis can be performed according to the method described in International Publication No. WO89/06970 supra. During this hydrolysis, one or more hydrolases selected from, for example, acid proteases, neutral proteases or alkaline proteases may be used.

In order to hydrolyze a globin protein, for example, a globin protein containing material is dispersed in water to give a solid content of 5–30% by weight. Then, this mixture is made acidic or basic to give an optimum pH for protease (s). Thereafter, protease(s) is(are) added to this mixture at once or gradually and reacted at 20–70° C. for 3–48 hours.

The resultant proteolysate is dried and caked as it is or after adding thereto an appropriate amount of filler such as carboxymethyl cellulose or dextrin. Thus, a proteolysate having an inhibitory effect of elevations of TG levels in blood can be obtained. This proteolysate contains the peptide of the invention at least 0.3% by weight.

Subsequently, the thus obtained proteolysate is purified. For this purification process, a known purification process may be employed. For example, ion exchange, ultrafiltration, reversed phase chromatography, etc. may be combined appropriately to purify those fractions containing the peptide of the invention. Although operations by means of ion exchange or ultrafiltration are not necessarily essential, it is preferable to incorporate them in the separation and purification process from the viewpoint that they can improve the degree of separation and purification. With respect to reversed phase chromatography, it is preferable to combine reversed phase chromatography under acidic and neutral conditions.

The amount of protein in a fraction can be determined by known methods for protein determination, e.g., the ninhydrin method. The amino acids sequences for the selected fractions can be identified by known methods and thereby the presence of the peptide of the invention can be confirmed.

The peptide of the invention derived from the thus separated fraction can be used as an active component of an agent for inhibiting elevations of TG levels in blood. Also, the fraction itself may be used directly as an active component of the above agent.

A-2. Method for Preparing the Peptide of the Invention by Chemical Synthesis

The peptide of the invention can also be synthesized chemically by known peptide synthesis methods. For example, the azide method, the acid chloride method, the acid anhydride method, the mixed acid anhydride method, the DCC method, the active ester method, the carboimidazol method, the oxidation-reduction method, the DCC-additive (HOMB, HOBt, HOSU) method (see, for example, Schröder & Luhke, *The Peptide*, Vol. 1 (1966), Academic Press, New York, USA; or Izumiya et al., *Peptide Synthesis*, Maruzen Co., Ltd. (1975)) and the like may be given. These peptide synthesis methods may be performed in either solid phase or liquid phase synthesis.

In the peptide synthetic method described above, amino acids having a side chain functional group such as tyrosine and threonine are preferably protected in their side chain functional groups. As a protective group, known protective groups such as a benzyloxicarbonyl group (Cbz-), t-butoxycarbonyl group (Boc-), benzyl group (Bz-), etc. may be used. This protective group can be removed by known methods in the process of synthesizing the peptide of the invention.

B. An Agent for Inhibiting Elevations of TG Levels in Blood

An agent for inhibiting elevations of TG levels in blood can be prepared using the peptide of the invention or the fraction containing the peptide (see A-1. above) as an active component.

As a carrier for the agent for inhibiting elevations of TG levels in blood, those excipients (such as fillers, extenders, binders, moisturizing agents, disintegrating agents, surfactants) or diluents which are conventionally used in the preparation of formulations depending on the form of use may be used. The form of a formulation is not particularly limited as long as the formulation effectively contains the peptide of the invention. For example, the formulation may be in a form of a solid agent such as tablets, powder, granules, pills; or in a form of an injection agent such as solutions, suspensions and emulsions. Alternatively, the agent of the invention may take a form of a dry product which can be made into a liquid form upon addition of an appropriate carrier before use. Any of these forms may be prepared by conventional methods.

The dose of the thus obtained agent for inhibiting elevations of TG levels in blood is appropriately selected depending on the method and form of administration of the formulation, conditions of the patient who receive the formulation, etc. Generally, a formulation containing the peptide of the invention at the ratio of about 0.001 to 80% by weight is prepared and, preferably, the formulation is administered so that the amount of the peptide of the invention administered is about 0.1 to 10 mg for one adult per day. The administration is not necessarily performed once a day. It may be performed 3 to 4 times a day.

The pharmaceutical formulations of various forms as described above may be administered through an appropriate administration route depending on the form. For example, the formulation in a form of an injection agent may be administered by intravenous, intramuscular, subcutaneous, intracutaneous, or intraperitoneal administration, etc. and the pharmaceutical formulation in a form of a solid agent may be administered by oral administration, etc.

C. A Specific Health Food

A food for specified health use (the so-called physiologically functional food) endowed with a function of inhibiting elevations of TG levels in blood can be prepared by using the peptide of the invention or the fraction containing the peptide (see A-1. above) as an active component. And the peptide of the invention can be used as a food additive of general foods.

The kinds of the above food are not particularly limited. The physiologically functional food may be applicable to milk, pudding, curry, stew, meat sauce, ham, cake, chocolate and the like. In particular, milk is preferable since it can facilitate the intake of the peptide of the invention which is difficult for infants to take directly because of the taste. Also, the addition of the peptide of the invention to foods such as cake and chocolate which essentially promote obesity is desirable from the viewpoint that obesity caused by the intake of the above foods can be prevented.

The amount of the peptide of the invention added to the physiologically functional food is appropriately selected depending on the kind of the food, the purpose of addition of the peptide of the invention, the effect expected to be produced by the intake of the food, etc. Generally, it is preferable to allow the food to contain the peptide of the invention so that about 0.5 to 5 mg of the peptide can be taken per one meal.

D. A Feed

A feed endowed with a function of inhibiting elevations of TG levels in blood in livestock, etc. can be prepared by combining in a feed the peptide of the invention or the fraction containing the peptide (see A-1. above) as an active component.

The feed in which the peptide of the invention is combined may be either a feed for livestock such as cows, pigs, chickens, etc. or a feed for hatchery fish such as sea breams, young yellowtails, etc.; the kind of the feed is not particularly limited. The amount of the peptide of the invention combined in a feed is appropriately selected depending on the kind of the feed, the effect expected to be produced by the intake of the feed, etc. Generally, it is preferable that the peptide of the invention be combined in a feed at the ratio of 0.01 to 0.5% by weight.

Since the agent for inhibiting elevations of TG levels in blood, the food for specified health use and the feed as described above have an action of cleaning lipid in blood, administration thereof can prevent or treat obesity and hyperlipemia of human or animals, and circulatory system disorders such as hypertension and arteriosclerosis associated with the above conditions. Furthermore, administration of the agent, etc. makes it possible to improve the meat quality of livestock and hatchery fish.

BRIEF DESCRIPTION OF THE DRAWINGS

FIG. 4 is reversed phase chromatograms of Val Val Tyr Pro (VVYP), Val Tyr Pro (VTP) and Val Thr Leu before the treatment with gastric juice, after the treatment with gastric juice and after the treatment with gastric/panereatic juices.

BEST MODE FOR CARRY OUT THE INVENTION

The present invention will be described more specifically below with reference to the following Examples, etc., which should not be constructed as limiting the technical scope of the present invention.

REFERENCE EXAMPLE

Preparation of a Globin Proteolysate

A method of preparation of a globin proteolysate using bovine erythrocytes will be described below in detail.

To 100 kg of fresh bovine erythrocytes, 250 liters of water was added to allow sufficient hemolysis. After adjustment of the pH to 2.8 with phosphoric acid, $2.6 \times 10^7$ units of acid protease from *Aspergillus niger* was added to the solution and reacted at 50° C. for 3 hr.

After the reaction, the reaction solution was heated at 80° C. for 30 min to terminate the reaction. Thereafter, an aqueous suspension of calcium hydroxide was added to the reaction solution to adjust the pH to 6.5. Then, 6.5 kg of diatomaceous earth was added and filtered with a filter press. The resultant filtrate was spray-dried to thereby obtain 23 kg of a globin proteolysate in a powder form. The molecular weight distribution of the resultant globin proteolysate was examined by gel filtration chromatography which was performed under the following conditions.

Equipment: High Performance Liquid Chromatograph (SHIMAZU CORP.; Model LC-6A)

Column: PolyHYDROXYETHYL A, 5 μm, 9.4×200 mm (PolyC Inc.)

Mobile phase: 50 mM formic acid

Flow rate: 0.5 ml/min

Detection: UV absorption at 221 nm

Figure 1:
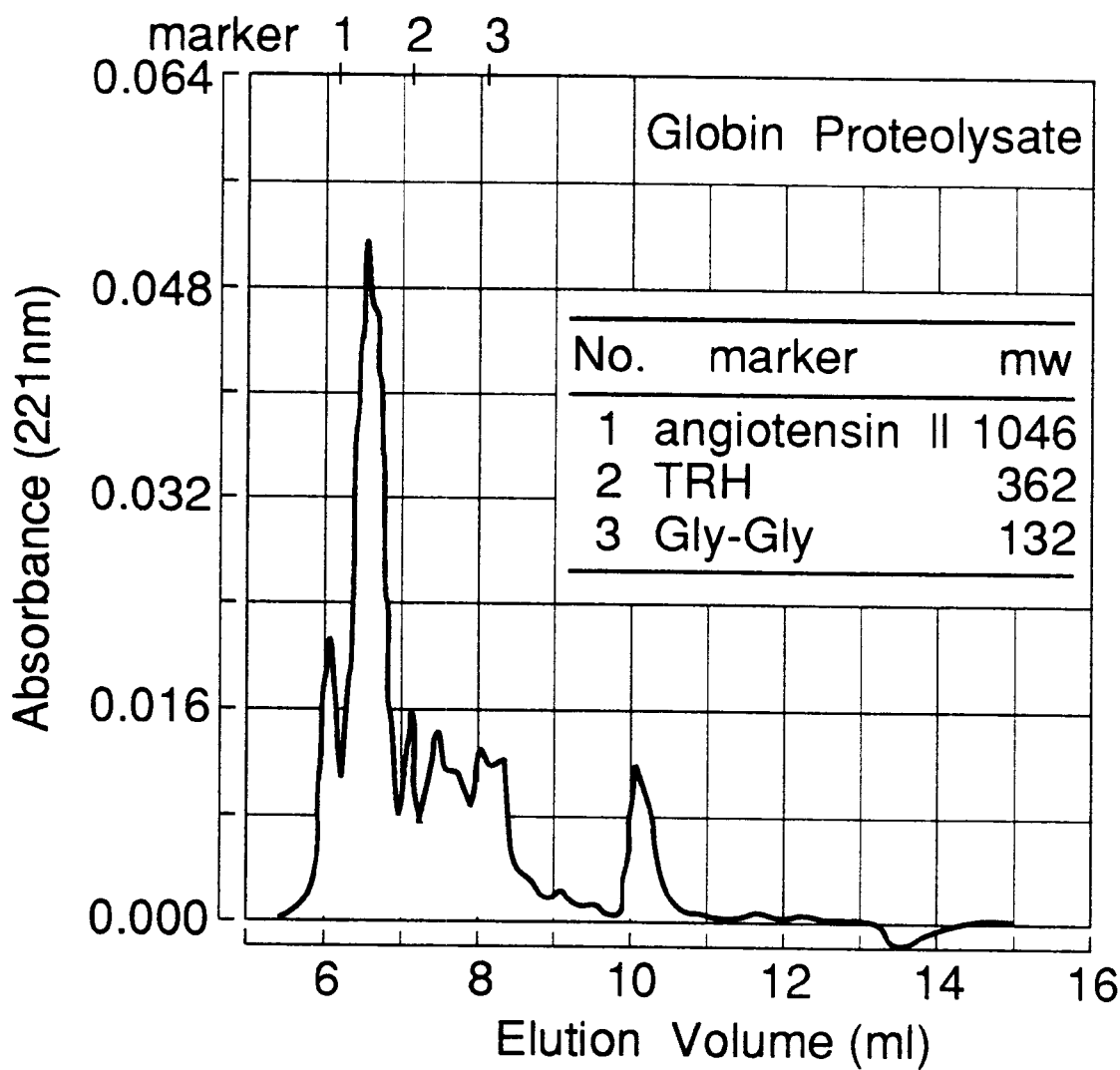
FIG. 1 is a gel chromatogram of a globin proteolysate.

The gel chromatogram of the globin proteolysate obtained by the above-described gel filtration chromatography is shown in FIG. 1.

EXAMPLE 1

Fractionation and Purification of a Peptide Inhibiting Elevations of TG Levels in Blood The peptide of the invention derived from protein was obtained through the procedures described below, i.e., (1) ion exchange, (2) ultrafiltration, (3) separation by reversed phase chromatography under acidic conditions and (4) separation by reversed phase chromatography under neutral conditions.

(1) Ion Exchange

A 10% by weight aqueous solution of 13.7 g of the globin proteolysate obtained in the Reference Example was added to a weakly acidic cation exchange resin (Amberlite $IRC_{50}$, $H^+$ form; JAPAN ORGANO CO., LTD.) and stirred for 1 hr to allow adsorption. Then, the unadsorbed fraction was obtained.

(2) Ultrafiltration

The unadsorbed fraction obtained by the ion exchange treatment was subjected to ultrafiltration using stirring type ultrafiltration equipment (Advantec; Model UHP 90K) and an ultrafiltration membrane (Advantec; UIIH-1; fraction molecular weight: 1000), and the remaining solution was collected.

The resultant fraction was quantitatively determined by performing the ninhydrin method after acid hydrolysis. The acid hydrolysis was performed by placing 1 ml of 6 N HCl at the final concentration against 3 to 5 mg of protein in a test tube, sealing the tube under atmospheric pressure and heating it at 110° C. for 22 hr. The ninhydrin method was performed as follows. The pH of the sample after the hydrolysis was adjusted to 5.0 with sodium hydroxide and then the sample was reacted with a ninhydrin reagent dissolved in 0.2 M citrate buffer (pH 5.0) at 100° C. for 15 min. Absorbance at 570 nm was measured. Separately, aqueous L-leucine solutions (0.75, 150, 225, 300 nmol/ml) were subjected to a ninhydrin reaction as standard solutions. Calibration curves were obtained from the absorbance measured, and the amount of amino groups in the sample equivalent to L-leucine was calculated. The results of the determination are shown in Table 1. The yield against the globin proteolysate used as a raw material is also shown in Table 1.

(3) Reversed Phase (Acidic) Chromatography

The remaining solution obtained by the ultrafiltration was subjected to reversed phase (acidic) chromatography under the following conditions.

Equipment: High Performance Liquid Chromatograph (SHIMAZU CORP.; Model LC-10A)

Column: SuperPac Pep-S, 15 μm, 22.5×250 mm (PHARMACIA K.K.)

Mobile phase: Aqueous acetonitrile solution containing 0.1% trifluoroacetic acid Gradient: Linear concentration gradient of 2–35% acetonitrile Acetonitrile concentration change 1%/min Flow rate: 5 ml/min Temperature: 40° C.

Detection: UV absorption at 220 nm

Preparative time: 53.8–54.5 min (Fraction A)

Figure 2:
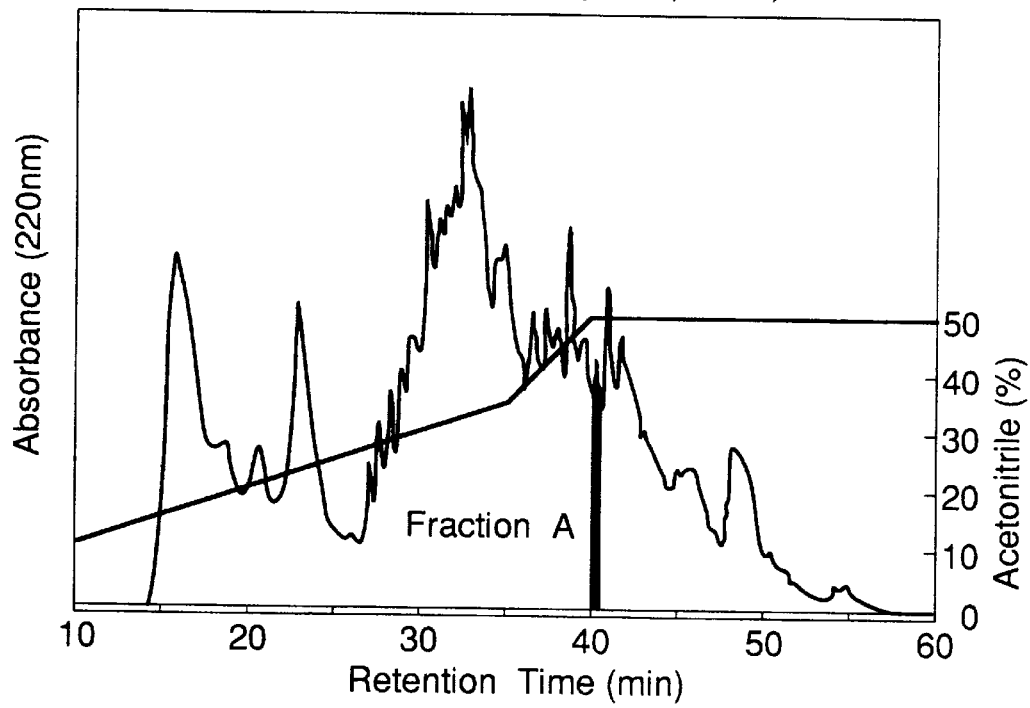
FIG. 2 is a reversed phase (acidic) chromatogram in Example 1.

The gel chromatogram obtained by the above-described reversed phase (acidic) chromatography is shown in FIG. 2.

The resultant fraction was quantitatively determined by performing amino acid analysis after acid hydrolysis. The acid hydrolysis was performed by placing 1 ml of 6 N HCl at the final concentration against 3 to 5 mg of protein in a test tube, sealing the tube under reduced pressure and heating it at 110° C. for 22 hr. The amino acid analysis was performed as follows under the conditions mentioned below.

Equipment: High Performance Liquid Chromatograph (SHIMAZU CORP.; Model LC-6A)

Column: Shim-pack ISC-07/S1504 Na, 7 μm, 4.0×150 mm (SHIMAZU CORP.)

Mobile phase: Amino Acid Mobile Phase Kit (Na type) from SHIMAZU CORP.

Flow rate: 0.3 ml/min

Temperature: 55° C.

Reaction solution 1: Analysis Kit OPA Reagent from SHIMAZU CORP.

Detection: Fluorescence absorption (Ex 348 nm, Em 450 nm)

The acid hydrolyzed solution was concentrated, dried and caked using a rotary evaporator, and dried further under reduced pressure for more than 12 hrs to thereby remove the HCl completely. Then, the resultant cake is dissolved in 0.2 M citrate buffer (pH 2.20) so that the content of each amino acid becomes about 100 nmol/ml. This solution was filtered through a 0.45 μm filter and 10 μl of the filtrate was applied on the column. On the other hand, as a standard solution, Amino Acid Mixed Standard Solution included 18 Components H-type (Wako Pure Chemical Industries, Ltd.) was diluted to 25-fold with 0.2 M citrate buffer (pH 2.20) and 10 μl of this dilution was applied to the column (each amino acid: 1 nmol/10 μl).

The calculated peak area of an amino acid was analyzed using Chromatopac C-R4A (SHIMAZU CORP.), and the amount of the amino acid was calculated from the peak area ratio of the sample and the standard solution. The results are shown in Table 1. The yield against the globin proteolysate is also shown in Table 1.

(4) Reversed Phase (Neutral) Chromatography

The fractions eluted and prepared in the reversed phase (acidic) chromatography were further subjected to reversed phase (neutral) chromatography under the following conditions.

Equipment: High Performance Liquid Chromatograph (SHIMAZU CORP.; Model LC-10A)

Column: SuperPac Pep-S, 15 μm, 22.5×250 mm (PHARMACIA K.K.)

Mobile phase: Aqueous acetonitrile solution containing 20 mM ammonium acetate buffer (pH 6.5)

Gradient: Linear concentration gradient of 0–25% acetonitrile Acetonitrile concentration change 0.5%/min Flow rate: 5 ml/min Temperature: 40° C.

Preparative time: 41.7–43.2 min (Fraction B) 45.8–51.0 min (Fraction C)

Figure 3:
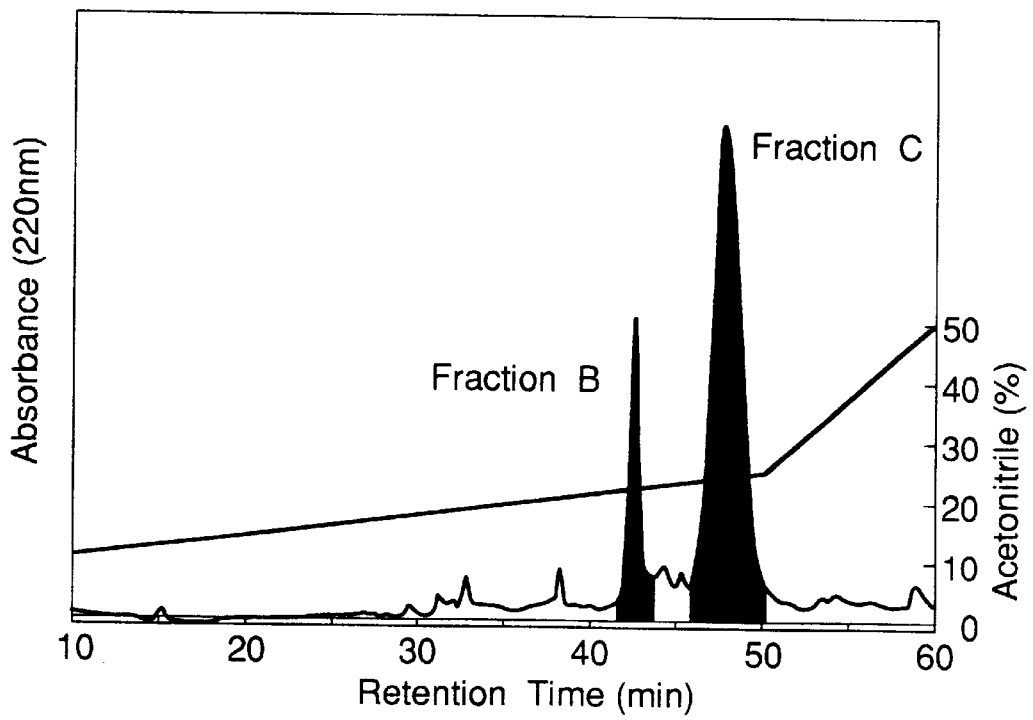
FIG. 3 is a reversed phase (neutral) chromatogram in Example 1.

The gel chromatogram obtained by the above-described reversed phase (neutral) chromatography is shown in FIG. 3.

The resultant fractions were quantitatively determined in the same manner as described in (3) above and identified. The amino acid composition was calculated from the ratio of each amino acid content to the total of amino acid contents. As a result, fraction B and fraction C were found to be VTL (Val-Thr-Leu) and VVYP (Val-Val-Tyr-Pro), respectively. Upon checking these sequences with the amino acid sequence of hemoglobin, it was confirmed that both sequences are present in the hemoglobin sequence.

The results of the quantitative determination are shown in Table 1 together with the yield against the globin proteolysate.

TABLE 1

| Peptide | Weight of Protein (g) | Yield (%) |
|---|---|---|
| Globin proteolysate | 13.7 | 100 |
| Ion exchange + Ultrafiltration Reversed phase chromatography | 4.24 | 30.9 |
| [Fraction A] | 0.39 | 0.28 |
| [Fraction B] VTL | 0.009 | 0.06 |
| [Fraction C] VVYP | 0.006 | 0.04 |

EXAMPLE 2

Synthesis of a Peptide Having the Amino Acid Sequence Shown in SEQ ID NO: 1

Val-Val-Tyr-Pro was synthesized with a SAM2 peptide synthesizer (Biosearch) according to the protocol of the synthesizer. Briefly, 2 g of acyloxymethyl resin to which 0.3 mmol of the 4th protective amino acid Boc-Pro-OH was linked per 1 g was set in the reactor of the above peptide synthesizer, and contacted with a deblocking solution containing 45% (v/v) trifluoroacetic acid (TFA), 2.5% (v/v) anisole and 52.5% (v/v) methylene chloride (DCM) for 20 min to thereby remove Boc groups. After washing with DCM, the resin was neutralized with DCM containing 10% (v/v) diisopropylethyleneamine and further washed with DCM. Thereafter, the resin was reacted in a mixed solution of 20 ml of DCM containing 4.0 mmol of diisopropylcarbodiimide (6.7 times each of theoretical equivalent) and dimethyl formamide (DMF) for 2 hr at room temperature. Then, the resin was washed with DMF and DCM in turn to thereby obtain Boc-Tyr(BrZ)-Pro-PAM resin.

According to a similar process, Boc-Val-OH was coupled twice. The thus coupled protected peptide resin was reacted in anhydrous hydrogen fluoride containing 10% (v/v) anisole at 0° C. for 1 hr. Then, hydrogen fluoride was removed and the resin was washed with ether. From the resultant mixture of peptides and resin, peptides were extracted with 50% acetic acid and lyophilized to thereby obtain about 250 mg of crude peptides.

The crude peptides were dissolved in 0.1% TFA and then developed in an Octadecyl Silica (ODS) column (Cosmosil $5C_{18}$, 250×20 mm: NACALAI TEAQUE INC.) with a linear concentration gradient of acetonitrile containing 0.1% TFA (20–70%/50 min, 10 ml/min). The peptide of interest was eluted at an acetonitrile concentration of about 50%.

TEST EXAMPLE 1

Effect (in vivo) of the Chemically Synthesized Peptide Inhibiting Elevations of TG Levels in Blood First, serum TG elevation inhibiting action was examined as described below on the globin proteolysate (GD) obtained in the Reference Example and the fraction obtained through the ion exchange and ultrafiltration in Example 1.

Olive oil (10 g/kg body weight) and an aqueous peptide solution (0.3 ml/mouse) were mixed in an injector to form a light emulsion, which was administered orally to male ICR mice (6 week old, body weight: 25–28 g) which had undergone an overnight fast. Two hours thereafter, blood was taken from the vena cava inferior under Nembutal anesthesia and serum TG levels were determined (Triglyceride G Testwaco; Waco Pure Chemical Industries, Ltd.). A dose-response curve was obtained from the dose of the peptide and inhibition rate of TG, and the 50% inhibition dose $ID_{50}$ so was calculated. Then, this was compared with the activity of the globin proteolysate (GD) determined in the same manner. The results are shown in Table 2.

TABLE 2

| Peptide | $ID_{50}$ [*1] (mg protein/mouse) | Specific Activity |
| --- | --- | --- |
| Globin proteolysate | 26 | 1 |
| Ion exchange + Ultrafiltration | 13 | 2 |

[*1] Dose which inhibits 50% of serum TG elevations in vivo.

From Table 2, it has been found that the serum TG elevation inhibiting activity of GD is enhanced if GD is treated with ion exchange resin followed by ultrafiltration to remove free amino acids.

Subsequently, serum TG elevation inhibiting action was examined as described below on the peptide (VVYP) having the amino acid sequence shown in SEQ ID NO: 1 synthesized in Example 2, peptides Val-Tyr-Pro (vYP) and Val-Thr-Leu (VTL) synthesized in the same manner as described in Example 2, and the globin proteolysate (GD) obtained in the Reference Example.

Olive oil (18 g/kg body weight) was administered orally to male ICR mice (6 week old, body weight: 25–28 g) which fasted for an overnight. One hour thereafter, an aqueous solution of the above peptide (0.3 ml/mouse) was administered orally. Another 1 hr thereafter, blood was taken from the vena cava inferior under Nembutal anesthesia and then serum TG levels were determined (Triglyceride G TestWako; Wako Pure Chemical Industries, Ltd.). A dose-response curve was obtained from the dose of the peptide and inhibition rate of TG, and the 50% inhibition dose $ID_{50}$ was calculated. Then, the activity of individual peptides was compared with each other. The results are shown in Table 3.

TABLE 3

Serum TG Elevation Inhibiting Action in Globin Proteolysate and Synthetic Peptides

| Peptide | Peptide Content Determined(%) | Peptide Content Theoretical(%)[*2] | $ID_{50}$ [*1] (mg protein/ mouse) | Specific Activity |
| --- | --- | --- | --- | --- |
| Globin proteolysate | — | 100 | 26 | 1 |
| VTL | — | 0.51 | 0.05 | 448 |
| VYP | — | 0.58 | 0.02 | 1130 |
| VVYP | 0.37[*3] | 0.74 | 0 | 6500 |

[*1] Dose which inhibits in vivo 50% of serum TG elevations.
[*2] Weight ratio calculated from the amino acid sequence of hemoglobin.
[*3] The value of Val-Val-Tyr-Pro in GD determined from the HPLC peak area.

As shown in Table 3, specific activity (ratio to mg protein) is 6500 in VVYP, 1130 in VYP and 448 in VTL. Thus, a remarkably stronger activity than that of GD is observed in all of these three peptides. Among all, VVYP was found to have a high activity 6500 times as much as the activity of GD.

From the results described above, it was suggested that the active component of fat absorption inhibiting action in globin proteolysate is likely to be the tetrapeptide VVYP.

TEST EXAMPLE 2

Stability (in vitro) of Chemically Synthetized Peptides Inhibiting Elevations of TG Levels in Blood against Digestive Enzymes In vitro stability test against digestive enzymes was conducted on the peptide (VVYP) having the amino acid sequence shown in SEQ ID NO: 1 synthesized in Example 2 and peptides Val-Tyr-Pro (VYP) and Val-Thr-Leu (VTL) synthesized in the same manner as described in Example 2.

Briefly, to 127.5 ml of 0.1 N HCl solution of the above VVYP, VYP or VTL, 22.5 ml of 0.67 mg/ml pepsin (artificial gastric juice) dissolved in 0.1 N HCl was added and reacted at 37° C. for 4 hr. Thereafter, 75 ml of 0.53 mg/ml pancreatin (artificial pancreatic juice) dissolved in 30 ml of 0.5 N borate buffer (pH 8.0) was added thereto and reacted at 37° C. for 2 hr. Samples before digestion with artificial gastric juice, after digestion with artificial gastric juice, and after digestion with artificial pancreatic juice were analyzed under the following conditions.

Equipment used: HPLC (Waters; LC Module1)
Column: SuperPac Pep-S, 5 µm (PHARMACIA K.K.)
Mobile phase A: 0.1% trifluoroacetic acid B: Acetonitrile-water (50:50, containing 0.1% tri-fluoroacetic acid)
Flow rate: 0.8 ml/min (VYP, VTL), 0.4 ml/min (VVYP)
Detection wavelength: 220 nm
Temperature: room temperature
Amount applied: 20 µl of 50-fold dilution The reversed phase chromatogram obtained by the above HPLC is shown in FIG. 4. The retention time and peak area of the digest are shown in Table 4.

TABLE 4

Effects of Gastrointestinal Digestion on the Peptides

| Treatment | Amount applied (mg) | VTL $t_R$ | VTL Area | VTL Ratio of recovery | VYP $t_R$ | VYP Area | VYP Ratio of recovery | VVYP $t_R$ | VVYP Area | VVYP Ratio of recovery |
|---|---|---|---|---|---|---|---|---|---|---|
| Before treatment | 1.02 | 30.44 | 110 | 100 | 27.02 | 1049 | 100 | 66.62 | 2828 | 100 |
| Gastric juice | 1.02 | nd | — | — | 27.68 | 1133 | 108 | 66.28 | 3058 | 108 |
| Gastric/Pancreatic juices | 0.60 | nd | — | — | 27.76 | 671 | 109 | 66.39 | 1675 | 101 |

Flow rate of the mobile phase in HPLC: VVYP 0.4 ml/min; VYP & VIL 0.8 ml/min $t_R$: retention time (min), Area: peak area (mV·sec), nd: not detected As is clear from FIG. 4 and Table 4, the peak of VTL disappeared after the digestion with artificial gastric juice, but the peaks of VYP and VVYP remained after the digestions with artificial pancreatic juices. From these results, a possibility has been suggested that the peptide VVYP of the present invention moves not only to the digestive tract lumens but also to small intestine mucosal cells and the circulation to manifest its effect without undergoing degradation by digestive enzymes in the digestive tract.

TEST EXAMPLE 3

Toxicological Study of the Peptide of the Invention

The peptide (VVYP) having the amino acid sequence shown in SEQ ID NO: 1 synthesized in Example 2 was administered orally to male and female ICR mice in an amount of 10 g/kg body weight or more (maximum possible dose). As a result, no death occurred.

EXAMPLE 3

Preparation of Foods Containing the Peptide of the Invention (1) Preparation of Milk Powder To 100 g of milk powder for infants, 10 mg of the peptide (VVYP) having the amino acid sequence shown in SEQ ID NO: 1 synthesized in Example 2 was added to thereby prepare a milk powder having a function of inhibiting elevations of TG levels in blood.

(2) Preparation of Chocolate

To 100 g of chocolate, 50 mg of the peptide (VVYP) having the amino acid sequence shown in SEQ ID NO: 1 synthesized in Example 2 was added to thereby prepare a chocolate having a function of inhibiting elevations of TG levels in blood.

EXAMPLE 4

Preparation of a Feed Containing the Peptide of the Invention

To a premix comprising vitamins, minerals, etc., the peptide (VVYP) having the amino acid sequence shown in SEQ ID NO: 1 synthesized in Example 2 was combined at the rate of 0.1% by weight. The resultant mixture was added to a commercial feed for hatchery fish at the rate of 10% by weight to thereby prepare a feed for hatchery fish having a function of inhibiting elevations of TG levels in blood.

Industrial Applicability

According to the present invention, a peptide inhibiting elevations of triglyceride levels in blood; an agent for inhibiting elevations of triglyceride levels in blood comprising the peptide as an active component; a food for specified health use (the so-called physiologically functional food) endowed with a function of inhibiting elevations of triglyceride levels in blood; and a feed endowed with a function of inhibiting elevations of triglyceride levels in blood are obtained. With these materials, it becomes possible to prevent or treat obesity and hyperlipemia of human or animals, and circulatory diseases such as hypertension and arteriosclerosis associated therewith. Furthermore, it becomes possible to improve the meat quality of livestock and hatchery fish.

We claim:

1. A peptide consisting of the amino acid sequence shown in SEQ ID NO: 1.

2. A pharmaceutical formulation for inhibiting elevations of triglyceride levels in blood comprising, as an active component, a peptide consisting of the amino acid sequence of claim 1.

3. A food which is endowed with a function of inhibiting elevations of triglyceride levels in blood comprising, as an active component a peptide consisting of the amino acid sequence of claim 1.

4. A feed which is endowed with a function of inhibiting elevations of triglyceride levels in blood comprising, as an active component, a peptide consisting of the amino acid sequence of claim 1.

5. A method for preventing or inhibiting elevations of triglyceride levels in blood of human or animals, comprising administering a prophylactically or therapeutically effective amount of peptide consisting of the amino acid sequence of claim 1.

6. A method for preventing or inhibiting obesity in human or animals, comprising administrating a prophylactically or therapeutically effective amount of peptide consisting of the amino acid sequence of claim 1.

7. A method for preventing or treating hyperlipemia in human or animals, comprising using a prophylactically or therapeutically effective amount of peptide consisting of the amino acid sequence of claim 1.

8. A pharmaceutical formulation comprising a prophylactically or therapeutically effective amount of the peptide consisting of the amino acid sequence shown in SEQ ID NO:1 to inhibit elevation in triglyceride levels in the blood of a human patient.

9. The pharmaceutical formulation of claim 8 being chosen from the group consisting of tablets, powder, granules, pills, or injectable form.

10. The pharmaceutical formulation of claim 9 wherein said injectable form is chosen from the group consisting of solutions, suspensions and emulsions.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: Bos frontalis

<400> SEQUENCE: 1

Val Val Tyr Pro